United States Patent [19]

Ott

[11] Patent Number: 4,834,091

[45] Date of Patent: May 30, 1989

[54] INTRAUTERINE FALLOPIAN TUBE OSTIAL PLUG AND SURGICAL PROCESS

[76] Inventor: Douglas E. Ott, P.O. Box 4383, Macon, Ga. 31208

[21] Appl. No.: 37,215

[22] Filed: Apr. 10, 1987

[51] Int. Cl.$^4$ .............................................. A61B 17/36
[52] U.S. Cl. .................................. 128/303.1; 128/820
[58] Field of Search ............ 128/1 R, 130, 341, 303.1, 128/395–398; 604/55

[56] References Cited

U.S. PATENT DOCUMENTS

| | | |
|---|---|---|
| Re. 29,345 | 8/1977 | Erb . |
| 872,978 | 12/1907 | Taggart . |
| 2,420,851 | 7/1943 | Zahn et al. . |
| 2,639,478 | 12/1949 | Nies et al. . |
| 2,822,592 | 2/1958 | Wendt . |
| 3,422,813 | 1/1969 | Braley et al. . |
| 3,675,639 | 7/1972 | Cimber . |
| 3,680,542 | 8/1972 | Cimber . |
| 3,687,129 | 8/1972 | Nuwayser . |
| 3,855,996 | 12/1974 | Bolduc . |
| 3,858,571 | 1/1975 | Rudolph .............................. 604/55 |
| 3,918,431 | 11/1975 | Sinnreich . |
| 4,160,446 | 7/1979 | Barrington . |
| 4,185,618 | 1/1980 | Corey . |
| 4,245,623 | 1/1981 | Erb . |
| 4,503,854 | 3/1985 | Jako .................................. 128/303.1 |
| 4,509,504 | 4/1985 | Brundin . |
| 4,606,336 | 8/1986 | Zeluff ................................. 128/130 |

FOREIGN PATENT DOCUMENTS 2530140 1/1984 France ................................ 128/130

OTHER PUBLICATIONS

"Sterilization with Silicone Plug: 30-Min. Hysteroscopic Procedure", Joseph Hixson.
"Experiences with the P Block, A Hydrogelic Tubal Blocking Device", Jan O. Brundin, pp. 251–265.
"Methods for Improving Tubal Ostial Observation, Obturation, and Perfusion with the Hysteroscope", Theodore P. Reed, III, et al., pp. 266–268.
"Hysteroscopic Sterilization by Silastic Plugs", Michael S. Baggish, pp. 269–274.
"Hysteroscopic Sterilization with Silicone Rubber: A Review of 3½ Years Experience", Joris F. D. E. De Maeyer, pp. 275–276.
"Hysteroscopic Tubal Sterilization and Formed-in-Place Silicone Rubber Plugs: Cause, Significance, and Prevention of Abnormal Plugs", Jay M. Cooper, Richard Houck; pp. 278–284.
"Photodynamic Ablation of the Endometrium with the Nd: YAG Laser Hysteroscopically as a Treatment of Menorrhagia", Daniell, et al., pp. 43–46.
"Hysteroscopic Laser Surgery Breaks New Ground", James F. Daniell, MD, pp. 82–92 and 99.
"Laser Photovaporization of Endometrium for the Treatment of Menorrhagia", Milton H. Goldrath, MD, et al., pp. 14–19.
*Application for an Investigational Device Exemption*, Informed Consent (Clincal Research Study).

Primary Examiner—Max Hindenburg
Attorney, Agent, or Firm—Bacon & Thomas

[57] ABSTRACT

The present invention provides for an improved surgical technique of the type which uses a Nd:YAG laser to treat the uterus while the uterus is kept distended by the flow of saline into the uterine cavity. The improvement comprises the hysteroscopic insertion of a retrievable ostial plug into the tubal ostia of each fallopian tube so that the saline does not flow through the fallopian tubes during the period of time in which the laser is used to treat the uterus. At the conclusion of the laser treatment, the retrievable ostial plugs are hysteroscopically retrieved and withdrawn. The invention also provides for a specific retrievable ostial plug for use in the procedure. The plugs are specifically adapted for hysteroscopic insertion and withdrawal from the tubal ostia.

9 Claims, 2 Drawing Sheets

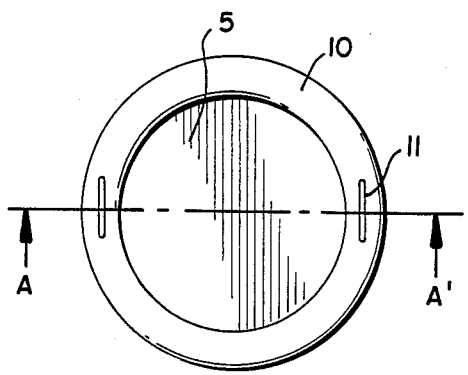
FIG. 5
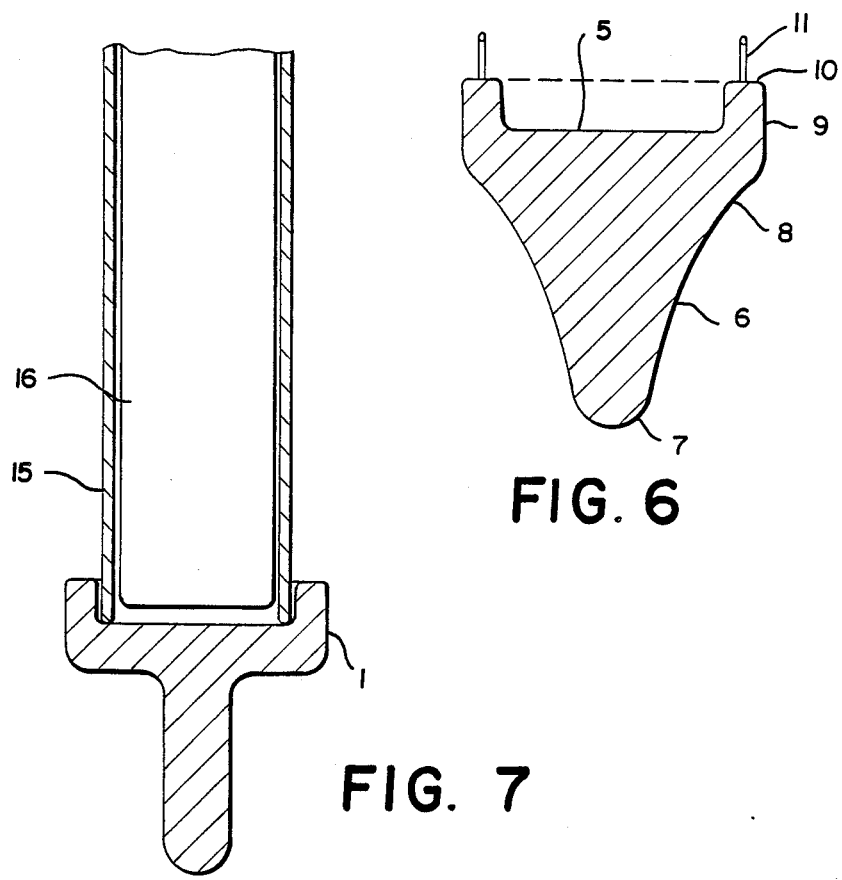
FIG. 6
FIG. 7

INTRAUTERINE FALLOPIAN TUBE OSTIAL PLUG AND SURGICAL PROCESS

BACKGROUND OF THE INVENTION

1. Field of the Invention

The present invention relates to the field of surgery for the treatment of disorders which occur in the uterus of female mammals, especially humans. More specifically, the invention relates to a particular surgical process which utilizes a laser to treat the diseased tissue in the uterus and also to a fallopian tube ostial plug which is used in the surgical procedure.

2. Background Information

In the treatment of diseases of the uterus, particularly in the treatment of menorrhagia, it is desirable to destroy the endometrium. Menorrhagia is a condition which occurs in certain diseases, which affects the endometrial lining of the uterus. The condition results in excessive menstrual flow or bleeding. In the treatment of the uterus, particularly in the treatment of menorrhagia, it is desirable to destroy the endometrium by means of photocoagulation. Typically, a laser is used to cause the photocoagulation of the endometrium. After the endometrium has been destroyed by photocoagulation, the menorrhagia is sufficiently decreased or even eliminated without the necessity of resorting to a more drastic surgical procedure such as a hysterectomy.

The Nd:YAG laser is particularly well suited for permanent destruction or ablation of the endometrium by photocoagulation. The term Nd:YAG is an abbreviation for neodymium-yttrium aluminum garnet.

The Nd:YAG laser procedure is conducted hysteroscopically, i.e., is conducted with an hysteroscope so that the procedure can be visually observed. In Nd:YAG hysteroscopy, delivery is by flexible, coated, fiber optic cable with saline used for uterine distension. The entire endometrium is photocoagulated from each cornu down to the internal cervical canal. The fiber tip is placed just off the endometrial surface and moved outward concentrically. Firing the laser results in visible blanching of the endometrium with tissue destruction extending downward to a depth of about 3-4 millimeters which is deep enough to penetrate the basalis layer and enter the muscularis and thereby destroy the regenerating portion of the endometrium.

An important part of the procedure involves the flushing of the uterine cavity to provide distension and visibility during the process; to function as a heat sink to avoid overheating and to wash out any blood and debris produced by firing the laser. As a result of the use of saline in this manner, the procedure inherently exposes the patient to the risk of fluid absorption or even fluid overload since the saline can enter the body cavity via the fallopian tubes. The fluid overload may result in edema or swelling due to the body's absorption of the saline. Absorption of a sudden infusion of extravascular fluid is particularly troublesome in patients who are anemic or who have cardiac or renal disease since they are particularly sensitive to changes in body fluid levels and electrolyte balance. Thus, a desirable improvement in the area of intra-uterine hysteroscopic Nd:YAG laser procedures would involve the reduction or elimination of extravascular fluid absorption and the risk of fluid overload.

In all of the prior art methods for carrying out ablation of the endometrium with a Nd:YAG laser, it has been observed that a significant amount of saline vascular absorption occurs and in many cases there is clinical vascular fluid overload.

In a method described in a publication by Milton Goldrath et al, entitled "*Laser Photovaporization of the Endometrium for the Treatment of Menorrhagia*" (American Journal of Obstetrics and Gynecology; vol. 140; No. 1; May 1, 1981; pp 14-19) it was noted that patients who have undergone the laser photovaporization of the endometrium, have shown evidence of fluid overload. This occurred even though an additional surgical technique (laparoscopy) was used to apply a Yoon ring to the fallopian tubes to patients who have not had prior sterilization. Apparently, the laparoscopic application of a Yoon ring to the fallopian tubes failed to avoid fluid absorption and fluid overload since some patients showed clinical signs of fluid overload. In addition, the laparoscopic procedure required an incision and thereby subjects the patients to additional obvious risks. Thus, Goldrath's procedure exposes patients to the risks of fluid overload and additional risks due to the incision.

In a publication by James F. Daniell, entitled "*Hysteroscopic Laser Surgery Breaks New Ground*" (Contemporary OB/GYN Special Issue; Update on Surgery, 1985; pp 82-99) it is stressed that fluid overload is a genuine risk in hysteroscopic laser procedures performed in the uterus. It is not surprising, therefore, that current consent forms which are signed by patients who are about to undergo the Nd:YAG procedure, acknowledge their understanding that the patient may absorb some of the irrigating solution and become edemateous and require treatment with an intraveneously administered diuretic.

More recently, this procedure has also been described in an article by James Daniell et al entitled "*Photodynamic Ablation of the Endometrium with the Nd:YAG Laser Hysteroscopically as a Treatment of Menorrhagia*" (Colposcopy and Gynecologic Laser Surgery; vol. 2, No. 1; published by Mary Ann Libert, Inc.; 1986; pp 43-46). In this procedure it is also recognized that the Nd:YAG laser surgical procedure results in the risk of fluid absorption and fluid overload. It is stated by the authors that others, such as Goldrath, have reported fluid overload and, in their own experience, there was significant saline vascular absorption which ranged from 100-800 cc with an average of 300 cc being absorbed. It was also noted by Daniell, that in his procedure, the patients who were not previously sterilized were subjected to a laparoscopic tubal occlusion procedure prior to the hysteroscopic laser procedure, to assure that all the patients were sterilized. Thus, Daniell, like Goldrath, requires an incision due to the laparoscopic procedure. Daniell also observes a significant fluid absorption level.

Daniell et al also note that another surgeon (Lamano) has reported that the laser surgical procedure results in a large amount of fluid absorption (600-4800 cc). It was further reported that the large absorption was similar in patients who underwent a preliminary tubal ligation and in patients who did not undergo tubal occlusion.

It has been stressed by workers in this field that tubal occlusion was undertaken as a preliminary step in these laser operations, and FDA protocol required it to preclude the possibility of fertilization from occurring after the procedure was completed. Thus, it was not considered desirable to remove the tubal occlusion since such removal would enhance the risk of future fertilization which was to be avoided.

More recently, Daniell et al have found that achieving sterility by means of tubal occlusion is unnecessary as a prerequisite in the procedure. In fact, it has been recently concluded by Daniell that tubal sterilization should not be a prerequisite for performing the procedure because the laser procedure resulted in sterilization anyway. Thus, it would be unnecessary and unwise to subject a patient to a preliminary laparoscopic tubal occlusion procedure. In addition, tubal occlusion as practiced in the prior art did not minimize or eliminate fluid absorption since there was a significant amount of fluid absorption in patients who had a preliminary tubular occlusion as well as in those who did not have a preliminary tubal occlusion. Thus, Daniell et al have concluded that tubal sterilization should not be a prerequisite for performing endometrial ablation with a laser if the only reason for tubal occlusion was to reduce the risk of saline intravascular absorption.

It will thus be observed that the prior art teaches that either the preliminary tubal sterilization by means of tubal occlusion should not be reversed or, as later discovered, it should be avoided altogether.

An additional problem associated with Nd:YAG laser surgery, is the risk of infection, especially peritonitis, if fluid were to enter the body cavity through the fallopian tubes during the procedure. Thus, a procedure which minimizes or avoids passage of fluid through the fallopian tubes into the body cavity will minimize or avoid the risk of infection as well as the risk of fluid overload.

The individual skill of the surgeon is also a factor which contributes to the risk of fluid overload and infection. The longer it takes a surgeon to complete the procedure, the longer the patient will be subjected to the flow of saline into the uterus. Consequently, surgeons who are relatively inexperienced in conducting this surgery may be subjecting their patients to greater risk than surgeons who have perfected their technique since the more experienced surgeons can complete the procedure in a relatively shorter period of time. Even experienced surgeons may occasionally require additional time to complete the procedure because of complications which may occur while the surgery is in progress. Thus, it would be beneficial to be able to minimize the above mentioned risks when the surgery takes a longer period of time to photocoagulate the endometrium.

SUMMARY OF THE INVENTION

The present invention relates to a Nd:YAG surgical procedure for treating diseases of the uterus. In particular, the invention provides an improved process for ablating or photocoagulating the endometrial lining of the uterus with a Nd:YAG laser. The invention also pertains to a particular type of ostial plug which is used in the procedure, the use of which comprises the improvement over the prior art surgical procedures.

The ostia plugs are made of conventional materials such as plastic which is suitable for body contact. The plugs are small for hysteroscopic insertion into the fallopian tubes at the point where the tubes open to the uterus. Means is provided on the plugs for easy removal of the plug immediately after the laser treatment has been completed in the uterus. Typically, one or more retrieval loops are provided for this purpose.

The process involves insertion of a retrievable ostial plug into the opening of each fallopian tube at the intrauterine tubal ostia. Placement of the ostial plugs is performed via direct visual observation with a hysteroscope. While the plugs are in place, an Nd:YAG laser is used to ablate or photocoagulate the diseased tissue in the uterus, especially the endometrial lining of the uterus. A conventional hysteroscopic procedure is used to apply the light from the laser to the diseased tissue. The conventional Nd:YAG procedure requires flow of saline into the uterus. While the plugs are in place, the saline is prevented from entering the fallopian tubes and, thus, the saline liquid is prevented from passing through the tubes and into the abdominal body cavity. The placement of the retrievable ostial plugs into the opening of the fallopian tube at the intrauterine tubal ostia, allows the surgeon an extended period of time to complete the surgery wihout the risk of fluid absorption, fluid overload or infection.

When the treatment with the laser is concluded, the plugs are retrieved by direct visualization through the hysteroscope by grasping the retrieval loop attached to the ostia plugs and withdrawing the plugs.

If laser treatment is required at the location of the plugs, then one plug is removed and that location is treated with the laser while the other plug is left in place. Then the other plug is removed and that location is likewise treated with the laser.

The present procedure avoids the risks associated with a preliminary laparscopic procedure for causing sterility as a prerequisite before conducting the Nd:YAG procedure. Unlike the prior art methods, no preliminary tubal sterilization is required in the present process. Furthermore, the plugs do not act to sterilize the patient, since they are removed from the patient at the completion of the surgery. There is no suggestion in the prior art to remove the tubal occlusion during the laser process. In fact, the prior art teaches to the contrary since, in the prior art processes, the tubes are blocked for the purpose of avoiding pregnancy after the surgery, thus suggesting that any tubular occlusion device should be left in place.

It is an object of the present invention to provide an improved Nd:YAG laser procedure for treating the uterus which uses a retrievable ostial plug to minimize fluid absorption, fluid overload and infection.

It is a further object to avoid the preliminary surgical procedures for causing sterility as a prerequisite in a uterine Nd:YAG laser surgical procedure while minimizing fluid absorption, fluid overload and infection, through the use of the temporary placement of ostial plugs in the fallopian tubes during the procedure.

It is a further object to provide a uterine Nd:YAG laser surgical procedure wherein a fallopian tube occlusion device is hysteroscopically inserted and removed during the procedure.

It is a further object to provide a retrievable ostial plug for use in a uterine Nd:YAG laser surgical procedure.

BRIEF DESCRIPTION OF THE DRAWINGS

FIG. 5 is a top view of the plug shown in FIG. 4.

FIG. 6 is a cross sectional view taken along line A, A' in FIG. 5.

FIG. 7 is a cross sectional view of plunger delivery device together with an ostial plug in place.

DETAILED DESCRIPTION OF THE INVENTION (DRAWINGS)

Figure 1:
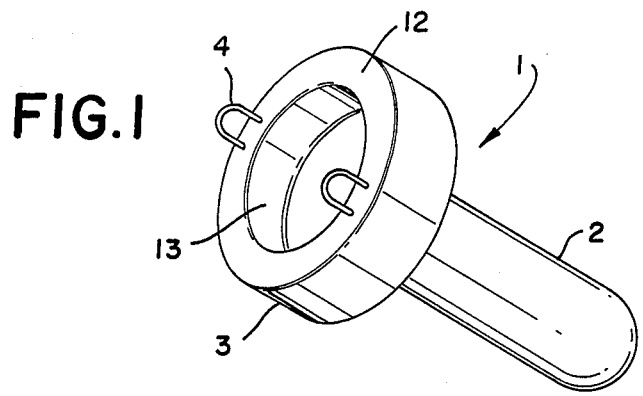
FIG. 1 is a perspective view of the retrievable ostial plug.

The surgical procedure is an improvement over conventional Nd:YAG laser hysteroscopy procedures which are used to photocoagulate the endometrium in the treatment of menorrhagia. Conventional Nd:YAG hysteroscopy procedures are well known to those skilled in the art and are described in the three publications identified herein which are authored by Milton Goldrath et al, James F. Daniell and James F. Daniell et al. These three publications are incorporated herein by reference since they describe the details of the procedure of which the present invention is an improvement.

The Nd:YAG laser procedure of which the present invention is an improvement, uses a Nd:YAG laser to destroy the endometrium by means of photocoagulation. This results in a photodynamic ablation of the endometrium and for that reason it is used in the treatment of mennorhagia. A suitable Nd:YAG device for use in this process is made by Cooper LaserSonics, Inc. and is sold and identified as Model 8000.

During the procedure fluid, preferably a liquid such as saline is constantly infused into the uterine cavity to provide distension and visibility; to act as a heat sink; and to wash out any blood and debris produced by firing the laser.

The improvement comprises the step of placing a retrievable ostia plug into the opening of each fallopian tube just before subjecting the diseased tissue to the laser and then removing the plugs from the tubes after the laser procedure has been concluded.

The placement of the ostia plugs is performed via direct visual observation with a hysteroscope. The plug may be mounted on a delivery device and transferred via either backloading the device by direct placement of the lug on a mounting device already placed through an operating channel of an operating hysteroscope or by direct placement (front loaded) onto a delivery device and passed in situ through the operating channel and placed at the tubal ostium. A conventional delivery device is used which is flexible and which is placed through an operative hysteroscope channel. The delivery device is capable of releasing the plug and seating it at the ostium.

Conventional hysteroscope delivery and retrieval devices may be used to insert and retrieve the ostial plugs. For this purpose, the ostial plugs are sized to fit the flexible Wolfe Hysteroscope 5 French and 7 French instruments Nos. 829.15, 828.17 and 829.17. In practice, the ostial plug is mounted on the tip of the loading device and the device is fed preloaded through the operating channel of the hysteroscope. Alternatively, the flexible Wolfe delivery device may be placed in the hysteroscope operating channel and the ostial plug mounted with the delivery device in situ (after loading). The hysteroscope instrument with the ostial plug device in place is then inserted through the cervix and into the uterus where the plug is placed into the tubal opening.

A loading device which is essentially in the form of a plunger may be used to place the ostial plug into the tubal opening. When using a plunger device, the ostial plug is again either placed on the loading device prior to placement in the operating sheath of the hysteroscope (preloaded) or after placement in the operating channel (after-loaded).

FIG. 1 shows a cross sectional view of a loaded plunger type of delivery device. The plunger delivery device comprises a flexible tube 15 having a plunger 16 located therein. The flexible tube is sized to fit snugly into the depression of the ostial plug. In FIG. 7, the plunger 16 is shown within the delivery device. The ostial plug is shown mounted onto the distal end of the delivery device with the internal portion, i.e., the plunger, retracted into the tube of the delivery device. When the ostial plug is placed at the intrauterine ostial opening, the plunger device is depressed, causing it to move toward the plug thereby releasing the mounted ostial plug by pushing it away from the tube and seating the ostial pug in the fallopian tube ostial opening. The plunger device is then removed and a second plug is mounted thereon and the procedure is repeated on the opposite side of the uterus at the other tubal opening.

At the completion of the laser surgery, the plugs may be removed by using a conventional hysteroscopic grasping instrument such as the Wolfe 7 French Flexible Sealed Grasping Forceps model No. 828.17, and the 7 French Flexible IUD Grasper model No. 827.17. The Wolfe Flexible Hysteroscope instrument No. 829.17 is particularly useful as amounting device for inserting the plug into place.

Once the plugs are in place the Nd:YAG laser is used in a conventional manner to destroy the diseased tissue in the uterus while saline is constantly infused into the uterus. Preferably the cervix will be distended somewhat to allow the saline to exit the uterus and thereby carry out the debris produced during the treatment. At the conclusion of the laser treatment, the plug is retrieved by direct visualization through the hysteroscope. Retrieval is accomplished by grasping the retrieval loop which is attached to the ostia plug. Once the plug has been grasped, it is withdrawn from the uterus.

In a preferred embodiment, the plugs are used for selective blocking and temporary occlusion of the tubal ostia areas. In this preferred embodiment, the plugs are inserted and then the laser is used to photocoagulate the endometrium. Following the photocoagulation of the endometrium, one of the plugs is removed from its respective fallopian tube and then the area which was masked and blocked by the plug and the tissue next to the plug is subjected to the laser so that any remaining endometrium or diseased tissue at that location is destroyed and the tissue at the tubal opening becomes photocoagulated. Next, the same procedure is carried out on the second tube by removing the plug therefrom and subjecting that area to the laser.

Before removing the second plug, the first plug may be reinserted into its respective tube so that only one tube remains unblocked at a time while treating the area occupied by the plugs. However, it is generally not necessary or desirable to reinsert the plug since laser treatment in the immediate vicinity of the area occupied by the plug requires very little time to complete. Generally, it takes less time to treat the second tube than it takes to reinsert the first plug. Consequently, it will take a shorter time to leave the first tube unplugged after it has been treated and then immediately proceed to treat the second tube without taking time to reinsert the first plug, than it would take to reinsert the first plug before proceeding to treat the second tube. Thus, there will be less risk of fluid overload if the surgeon leaves the first tube unplugged after it has been treated and immediately proceeds to complete the procedure by immediately treating the second tube.

It will be noted that in the preferred embodiment described above, a tube is left unblocked while being treated with the laser. Since the period of time required for treating this small tubal area is minuscule in comparison to the amount of time required to treat the main portion of the endometrial lining in the uterus, there is hardly any opportunity for fluid to pass through the tubes while they are left open for this brief period of time. Consequently, there is very little risk even when a surgeon takes a long time to treat the main portion of the endometrial lining in the uterus because the tubes remain blocked while the main portion of the endometrial lining is being treated.

While the above procedure has been described with reference to the specific laser photocoagulation of the endometrium to treat menorrhagia, the present invention is also suitable for other uterine surgical procedures which require the flow of fluid, preferably a liquid such as saline into the uterus. For example, the present invention could be employed in a procedure where a Nd:YAG laser is used to remove submucosal fibroids or uterine septa.

The retrieval ostial plug used in the above process is illustrated in FIGS. 1-6.

Figure 2:
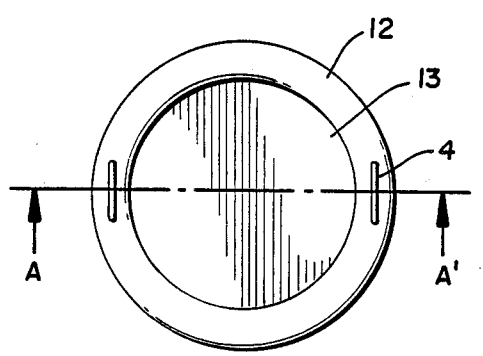
FIG. 2 is a top view of the plug shown in FIG. 1.
Figure 3:
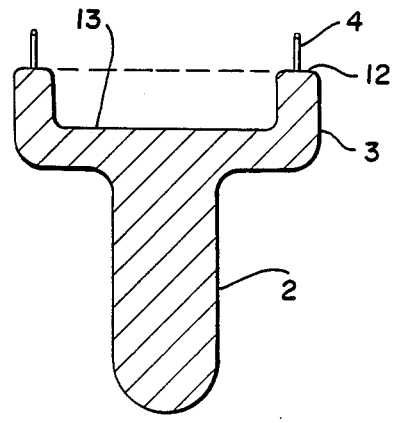
FIG. 3 is a cross sectional view taken along line A, A' in FIG. 2.

One embodiment of the retrievable ostial plug is shown in FIGS. 1-3. In the embodiment shown in FIGS. 1-3, the plug, shown generally by reference numeral 1, comprises an elongated occluding member 2 on one end and a relatively wide or flanged grasping member 3 on the other end. The occluding member is generally circular in cross section. The grasping member or segment may be formed by an increase in the diameter of the occluding member at one end thereof. One or more retrieval loops, preferably made of wire, are shown illustrated by reference numeral 4. In a preferred embodiment, two loops are used as shown in the Figures. The loops are embedded into the wide end of the plug. Preferably, the wide or flanged portion forms a circumferential lip 12 which is on the top of the flanged portion. In the center of the lip is a depression 13. The depression surrounded by the circumferential lip serves to enhance the occlusion of the tube due to the pressure of the saline against the depression while the plug is inserted in the tube.

The plug is sized so that the occluding member fits into the fallopian tube and the wide flanged portion remains exposed for quick and easy retrieval via the hysteroscope. Typically the plug shown in FIGS. 1-3 is about 4 millimeters long and about 4 millimeters wide, not including the length of the retrieval loops in these measurements. In a preferred embodiment, the retrieval loops are attached to the ring on top of the grasping segment. Preferably two retrieval loops are attached, one on either side of the depression.

Figure 4:
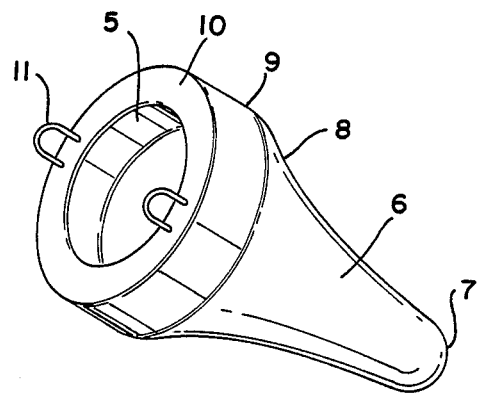
FIG. 4 is a perspective view of a second embodiment of the retrievable ostial plug.

A second embodiment is shown in FIGS. 4-6. The embodiment shown in FIGS. 4-6 is a modification of the plug shown in FIGS. 1-3. In the modified version, the occluding member is wider at the end nearest the grasping segment. The modified version comprises an elongated occlusion member 6 which is narrower at end 7 and wider at the other end 8 where it meets the relatively wide grasping portion 9. The occluding member 6 is generally circular in cross section. The wide portion of the occluding member may be as wide as the grasping member or portion 9. A circumferential lip 10 and depression 5, shown in FIGS. 4, 5 and 6, are analogous to the lip 12 and depressions 13 shown in FIG. 2. The retrieval plug shown in FIGS. 4-6 also contains one or more retrieval loops indicated by reference numeral 11. Typically a plug of the type shown in FIGS. 4-6 is about 5 millimeters long (not counting the retrieval loops) and about 3.5 millimeters wide. The precise dimensions of either embodiment of the plug can be varied and adapted to meet specific dimensional criteria required in the procedure.

The plug is preferably made of plastic or other suitable material. Any plastic which is suitable for surgical body contact may be used. The plastic is preferably compressible and has a significant tensile strength. Suitable plastics include silastic elastomer, which is available from Dow Corning and sold as "Silastic 382 Medical Grade Elastomer"; polyethylene; silicone rubber such as "MDX 4-4210" sold by Dow Corning; methylacrylate polymer; polyvinylpyrolidone; HP silicone elastomer; polytetrafluoroethylene such as Teflon, nylon, hydrogel silicone and silicone rubber. Preferably, the plugs are formulated with a conventional radiopaque material so that their presence can be determined by means of an X-ray.

Conventional molding processes may be used to form the plastic plugs. For example, the plugs of this invention may be formed by using the well known lost wax molding technique.

In making a plug, a plastic or chalk carving is first made into the exact size and shape of the plug. A lubrication material, such a Dilube, may be applied to the carving. Next, wax is melted over the lubricated carving and the wax is then removed from the carving which is now a wax mold. A small plastic tube is then attached to the wax mold. The wax with the tubing is encased in an investment material which hardens. It is then placed in an oven at approximately 1200° which burns away the wax and the investment material is left, forming an investment mold. Melted metal (usually a nickel and silver mixture) is forced into the burned out mold cavity. Time is allowed for hardening and the investment material is chipped away after the metal has hardened. This results in the formation of a metal mold. A suitable plastic in the form of a liquid or paste-like consistency is then poured into the mold and the retrieval loops are suspended in place. After the plastic has hardened, the device is then removed from the mold.

While the present invention has been described in terms of certain preferred embodiments, one skilled in the art will readily appreciate that various modifications, changes, omissions and substitutions may be made without departing from the spirit thereof. It is intended, therefore, that the present invention be limited solely by the scope of the following claims.

I claim:

1. In an intrauterine hysteroscopic Nd:YAG laser surgery procedure for photocoagulating diseased tissue in the uterus, said process being of the type which comprises the steps of hyteroscopically photocoagulating the uterus with a Nd:YAG laser while flowing fluid into the uterus; wherein the improvement comprises the steps of hysteroscopically inserting a first retrievable ostial plug into one tubal ostia of the uterus and a second retrievable plug into a second tubal ostia of the uterus so that the fluid will not flow through the fallopian tubes; flowing the fluid into the uterus while photocoagulating the diseased tissue in the uterus with the laser; withdrawing the first plug to expose a first ostia area and photocoagulating said first ostia area; and then withdrawing the second ostial plug and photocoagulating the second ostia area.

2. The method of claim 1 wherein the fluid is a saline solution.

3. The method of claim 2, wherein the endometrium is photocoagulated with the laser.

4. The method of claim 1, wherein the retreivable ostial plug comprises an occluding member which is generally circular in cross section and which is adapted for insertion into a fallopian tube; said occluding member being flanged on one end to provide a grasping segment, said grasping segment having a central depression on the top portion thereof formed by a circumferential lip on the top end grasping segment; and said grasping segment having at least one retrievable loop attached thereto.

5. In an intrauterine hysteroscope Nd:YAG laser surgery process for photocoagulating diseased tissue in the uterus, said process being of the type which comprises the steps of hysteroscopically photocoagulating the uterus with Nd:YAG laser while flowing fluid into the uterus; wherein the improvement comprises the steps of hysteroscopically inserting a retrievable ostial plug into each tubal ostia to prevent the flow of fluid therethrough; flowing the fluid into the uterus while photocoagulating the diseased tissue in the uterus with the laser and then retrieving and withdrawing each ostial plug from the uterus at the conclusion of the laser treatment for photocoagulating the diseased tissue.

6. The method of claim 5 wherein the fluid is a saline solution.

7. The method of claim 6, wherein the endometrium photocoagulated with the laser.

8. In a surgical procedure of the type which includes the step of flushing the uterine cavity with a saline solution during surgery, wherein the improvement comprises the steps of inserting a first retrievable ostial plug into one tubal ostia of the uterus and inserting a second retrievable ostial plug into a second tubal ostia of the uterus so that the saline solution will not flow into the fallopian tubes during the surgical procedure, and then removing the plugs at the completion of the surgical procedure.

9. In a surgical procedure of the type which includes the step of flushing the uterine cavity with a fluid during surgery, wherein the improvement comprises the steps of inserting a first retrievable ostial plug into one tubal ostia of the uterus and inserting a second retrievable ostial plug into a second tubal ostia of the uterus so that the fluid will not flow into the fallopian types during the surgical procedure, and then removing the plugs at the completion of the surgical procedure.

* * * * *